United States Patent [19]

Neumaier et al.

[11] 3,950,384

[45] Apr. 13, 1976

[54] PROCESS FOR THE MANUFACTURE OF NITRILOTRIACETONITRILE

[75] Inventors: Hubert Neumaier, Knapsack; Wilhelm Vogt, Efferen; Kurt Sennewald, Hermulheim; Richard Schüller, Cologne-Holweide; Günther Lenz, Frechen-Bachem, all of Germany

[73] Assignee: Hoechst Aktiengesellschaft, Frankfurt, Germany

[22] Filed: June 18, 1974

[21] Appl. No.: 480,524

Related U.S. Application Data

[63] Continuation of Ser. No. 133,978, April 14, 1971, abandoned.

[30] Foreign Application Priority Data

May 26, 1970 Germany.............................. 2025632

[52] U.S. Cl........................................... 260/465.5 A
[51] Int. Cl.².......................................... C07C 120/00
[58] Field of Search............................. 260/465.5 A

[56] References Cited
UNITED STATES PATENTS

| 3,337,607 | 8/1967 | Wollensak .................... 260/465.5 A |
| 3,840,581 | 10/1974 | Neumaier et al. ............ 260/465.5 A |
| 3,856,844 | 12/1974 | Wikman........................ 260/465.5 A |
| 3,862,203 | 1/1975 | Greco et al. .................. 260/465.5 A |

Primary Examiner—Joseph P. Brust
Attorney, Agent, or Firm—Connolly and Hutz

[57] ABSTRACT

Production of nitrilotriacetonitrile by reacting a salt of ammonia and a non-oxidizing acids with formaldehyde and hydrogen cyanide in an aqueous acid phase, at elevated temperature, completing the reaction and separating the reaction mixture into firstly crystalline nitrilotriacetonitrile and secondly an aqueous acid phase as the mother liquor. More particularly, a product obtained by primary reaction of an aqueous ammonium salt solution with an aqueous formaldehyde solution, the ammonium salt and formaldehyde being used in a ratio larger than 1:6, is reacted with a stoichiometric proportion of an aqueous hydrogen cyanide solution, the said stoichiometric proportion being based on the formaldehyde concentration of the primary reaction product.

8 Claims, 1 Drawing Figure

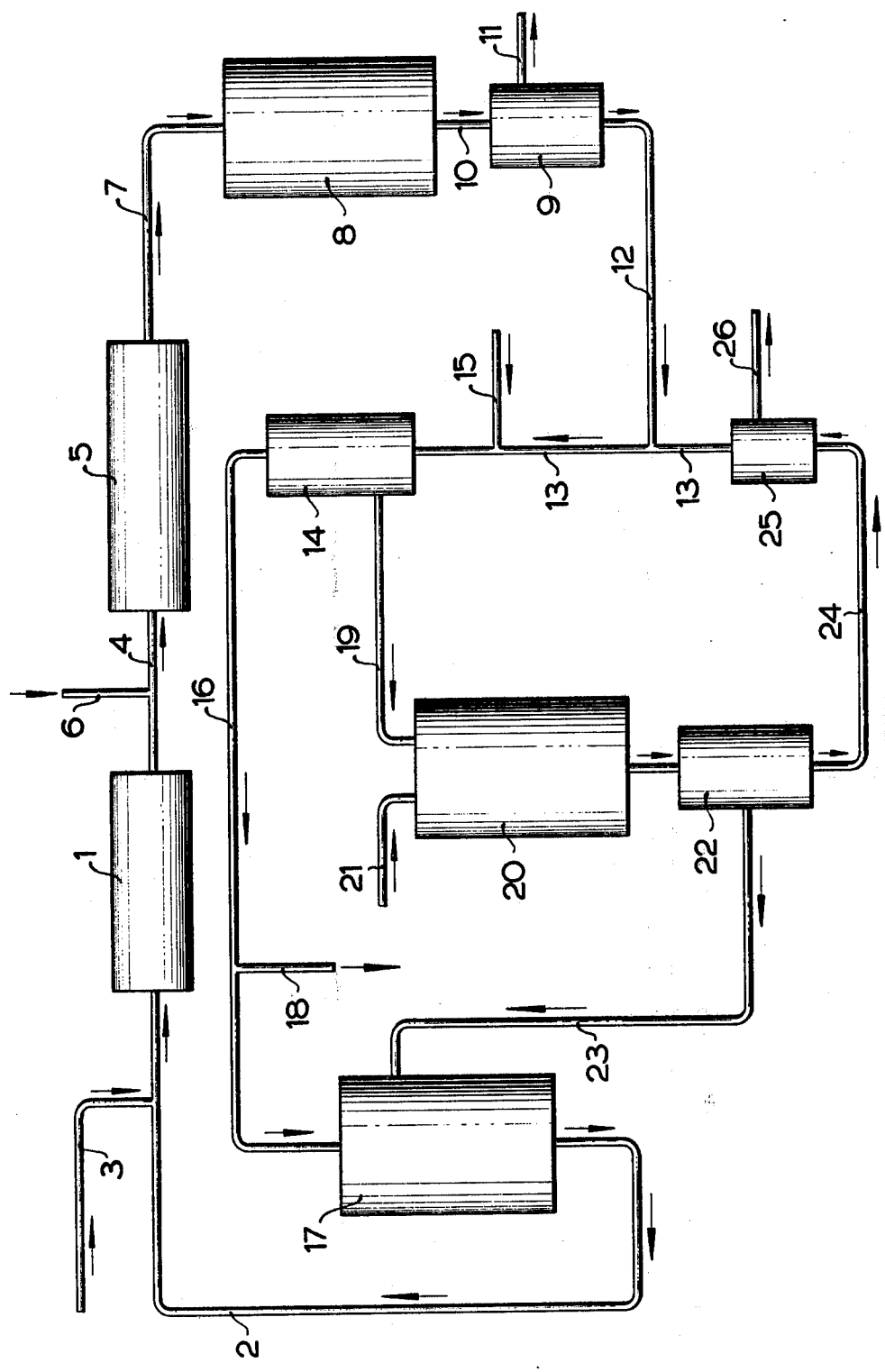

PROCESS FOR THE MANUFACTURE OF NITRILOTRIACETONITRILE

This application is a continuation of application Ser. No. 133,978, filed Apr. 14, 1971, and now abandoned.

The present invention relates to the production and more particularly to the continuous production of nitrilotriacetonitrile by reacting an ammonium salt with formaldehyde and hydrocyanic acid in an acid medium.

Nitrilotriacetonitrile has gained increasing technical and commercial interest during the last few years, as its saponification product, namely nitrilotriacetic acid and the salts thereof, finds widespread uses in the detergent industries, for dyeing textiles and in galvanization.

An earlier process for making nitrilotriacetonitrile has been described in German Pat. No. 694,780, wherein a solution of ammonium sulfate in formaldehyde of 30 percent strength is mixed, while cooling, with concentrated hydrochloric acid and an aqueous sodium cyanide solution of 24 percent strength is successively poured, with agitation, into the mixture so made. Following heat treatment, first for 20 hours to 40°C and then for a further 20 hours to 60°C, precipitated, crystallized nitrilotriacetonitrile is isolated from the solution. The step of maintaining the reaction mixture in an acid medium is an important requirement of this process for making nitrilotriacetonitrile as the reaction mixture has been found to undergo undesirable coloration in the alkaline range.

As to this requirement, however, the above process fails to be fully satisfactory. The reason for this resides in the fact that sodium cyanide is added to the starting mixture. As a result thereof, the hydrochloric acid present in the starting mixture is consumed with the resultant formation of hydrogen chloride, and the acidity of the solution continuously reduced. Too rapid a decrease of the concentration of acid and the eventual change of the pH-value of the reaction mixture to the alkaline region may give rise to the formation of undesirable organic byproducts and brown coloration of the reaction mixture. The need later to purify the product having inorganic salt contaminants therein is a further disadvantage of this earlier process. The salts are removed by washing the crude nitrilotriacetonitrile with water in which the salts are dissolved together with a nitrile fraction that is lost.

In the process described in German Pat. No. 1,112,081 hydrocyanic acid is substituted for the sodium cyanide in an attempt to obviate the disadvantageous phenomena reported above, wherein a liquid reaction mixture of equimolar proportions of formaldehyde and liquid or gaseous hydrocyanic acid is reacted with ammonia at a pH of between <3 and preferably <1, while maintaining the said pH, in such a manner that 1 mol of formaldehyde and 1 mol of hydrocyanic acid are used per each of the hydrogen atoms of the ammonia, the ammonia being added at a rate at which it substantially undergoes instantaneous and complete reaction with the resultant formation of nitrilotriacetonitrile, that is successively isolated in crystallized form. The acid necessary to establish the pH-value, for example sulfuric acid, is added in catalytic amounts to the starting mixture.

The small proportions of acid added in the process just described above hardly enable local overfeeding of ammonia in the reaction mixture and displacement of the pH-value to the alkaline region to be avoided. This effects coloration of the reaction mixture and contamination of the reaction product. The mere use of a pH-value of 2 to 3 gives already rise to the formation of traces of aminodiacetonitrile and methylene-bis-aminodiacetonitrile by-products, which are easy to demonstrate; these are compounds which decompose with brown coloration and considerably impair the quality of the resulting nitrilotriacetonitrile, at the reaction temperatures used. In an attempt to remedy this, it is suggested in German Pat. No. 1,112,081 that the reaction mixture be decolorized by means of activated charcoal. However, in order substantially to eliminate the inherent risk of by-product formation, it is necessary slowly to add ammonia to the reaction mixture, naturally at the price of long reaction periods. Needless to say the additional decolorization and slow addition of ammonia are non-beneficial steps. In view of this, it is highly desirable to have an improved process for making nitrilotriacetonitrile which firstly is free from the disadvantageous phenomena reported above and secondly can be carried out in continuous fashion.

A process for the continuous manufacture of nitrilotriacetonitrile has been described earlier in German published specification No. 1,805,404, wherein at least stoichiometric proportions of ammonia, formaldehyde and hydrogen cyanide are reacted in the presence of a mineral acid, at a temperature higher than 120°C, preferably 125°–135°C, and under a pressure of between 0.35 and 7 atmospheres (gauge), and resulting nitrilotriacetonitrile, which is substantially liquid, is delivered to a quenching zone for crystallization therein. A preferred embodiment of this process comprises subjecting ammonia and formaldehyde to a preliminary reaction to give hexamethylenetetramine and contacting the latter with further formaldehyde and hydrogen cyanide with the resultant formation of the nitrile. In this earlier process, the ammonia, formaldehyde and hydrogen cyanide reactants are allowed to remain in the reactor for a suggested period of between 1 and 30 minutes.

Despite this short sojourn time of the reaction mixture in the reactor, the fact remains that the high reaction temperature of more than 120°C makes it impossible in this process to obviate (a) undesirable formation of by-products or decomposition products which primarily effect yellow or brown coloration of the final product, or (b) undesirable partial and precocious saponification of the nitrile. In other words, the final product does not come up to the quality standards set by the users. On the other hand, it is taught in German published specification No. 1,805,404 that temperatures lower than 100°C, whereby by-product formation could at least be limited, make the yield decrease from initially 90 percent down to 70 percent of the theoretical, which is unacceptable from an economical point of view.

The present invention now unexpectedly provides a process for the continuous manufacture of very pure nitrilotriacetonitrile in yields of more than 90 percent from an ammonium salt of a non-oxidizing acid, formaldehyde and hydrogen cyanide under mild reaction conditions, i. e., at a reaction temperature of between about 50° and 110°C, which comprises carrying out the reaction in two process steps or two reactors which are series-connected together.

The process of the present invention for the manufacture of nitrilotriacetonitrile by reacting a salt of ammonia and a non-oxidizing acid with formaldehyde and hydrogen cyanide in an aqueous acid phase, at elevated temperature, completing the reaction and separating the reaction mixture into firstly crystalline nitrilotriacetonitrile and secondly an aqueous acid phase as the mother liquor, comprises subjecting a product obtained by primary reaction of an aqueous ammonium salt solution with an aqueous formaldehyde solution, the said ammonium salt and the said formaldehyde being used in a ratio larger than 1:6, to reaction with a stoichiometric proportion of an aqueous hydrogen cyanide solution, the said stoichiometric proportion being based on the formaldehyde concentration of the said primary reaction product.

The process of the present invention can be used with particular advantage for the continuous production of nitrilotriacetonitrile. This embodiment of the present invention comprises continuously supplying a preliminary reactor with an aqueous solution of the ammonium salt and an aqueous solution of formaldehyde, the ammonium salt being used in a stoichiometric excess of between 5 and 40 percent over the formaldehyde; thoroughly mixing the said aqueous solution components and reacting them inside the said reactor at a temperature of between about 50° and 110°C and within a period of between about 2 seconds and 4 minutes; delivering resulting reaction product to a second reactor series-connected to the said preliminary reactor and reacting the said reaction product in said second reactor with a stoichiometric proportion of hydrogen cyanide in an aqueous acid phase, for a period of a least 3 minutes, under a pressure of between 3 and 25 atmospheres (gauge) and at the temperature necessary to liquefy resulting nitrilotriacetonitrile; cooling the reacting mixture in the said second reactor with pressure relief down to atmospheric and precipitating the nitrilotriacetonitrile therefrom, and isolating the nitrilotriacetonitrile from the aqueous phase.

In carrying out the process of the present invention, it has been found advantageous to use a substantially saturated aqueous ammonium salt solution and an aqueous methanol-free formaldehyde solution with a strength of between about 20 and 55 weight percent, the ammonium salt being preferably used in a stoichiometric excess of between about 15 and 20 percent. The ammonium salts useful in the process of the present invention preferably include those of sulfuric acid, phosphoric acid or hydrochloric acid. Reaction temperatures of between about 60° and 70°C coupled with a 1–2 minute sojourn time of the reaction components in the preliminary reactor make the reaction proceed under very mild conditions, with reference to the formation of by-products.

The reaction in the second reactor, which is series-connected to the preliminary reactor, is preferably effected with the use of liquid hydrogen cyanide, or with the use of an aqueous solution having a strength of at least about 40 weight percent, the reactor being preferably maintained under a pressure of about 10 to 15 atmospheres (gauge) and at a temperature of between about 90 and 110°C. While the sojourn time of the reaction mixture in the second reactor is not as critical as that in the preliminary reactor, as regards by-product formation, the fact remains that the reaction mixture increasingly undergoes undesirable yellow or brown coloration in the case of unnecessary long sojourn times in the second reactor. To avoid this, the sojourn time in the second reactor should preferably be limited to a period of between about 3 and 20 minutes, more preferably 6 and 10 minutes.

Following termination of the reaction, the nitrilotriacetonitrile is isolated. To this end, the reaction mixture is taken from the second reactor and quenched by cooling it down to a temperature of between about 20° and 30°C with pressure relief down to atmospheric pressure, whereby the nitrile is precipitated from the reaction mixture. The nitrile may be isolated by subjecting the reaction mixture to filtration or centrifugation. Following this, the nitrile may be water-washed, if necessary or convenient, and it is dried.

A further embodiment of the process of the present invention comprises recovering the excess proportion of the ammonium salt used as well as the acid set free during the reaction, the acid being first transformed into its ammonium salt, and recycling the recovered components to the preliminary reactor. The excess proportion of the ammonium salt introduced into the reactor together with the starting materials, as well as the ammonium salt of the acid set free during the reaction, are recovered by mixing the aqueous phase freed from nitrilotriacetonitrile with a substantially equal proportion by volume of a saturated aqueous formaldehyde solution, which is the same as that used as starting material, and treating the resulting mixture under vacuum to evaporate water therefrom in a quantity by volume, which is substantially the same as that introduced into the process together with the starting materials and that formed in the process as reaction water. The liquid acid evaporation residue is treated with ammonia so as to establish a pH-value of at most 6, preferably 3 to 5, ammonium salt which commences to precipitate from the evaporation residue is separated therefrom, made into a suitable aqueous solution and then recycled to the preliminary reactor. The aqueous evaporation residue freed from solid ammonium salt is further freed from oily by-products originating from the reaction, and the remaining aqueous proportion is introduced together with fresh mother liquor freed from nitrilotriacetonitrile, into the evaporator.

Reactors, (preliminary and second reactors) very suitable for use in carrying out the process of the present invention include tubular coils, pipes or plate heat exchangers made up of chrome-nickel steel, nickel-molybdenum alloys or enamelled steel, of given dimensions.

The following statements further illustrate the process of the present invention.

The sojourn time of the reaction components in the preliminary reactor is one of the features vital to the present invention, as already mentioned earlier, because of its influence firstly upon the yield of nitrilotriacetonitrile and secondly upon the rate of by-product formation. The following Table 1 shows, for example, that the nitrilotriacetonitrile yield is a function of the sojourn time of the ammonium salt/formaldehyde-mixture in the preliminary reactor, at a reaction temperature of 70°C.

TABLE 1

| Sojourn time (minutes) | NTN-Yield (in percent of the theoretical) |
|---|---|
| <1 | <88 |
| 1 | 90 |
| 2 | 92.5 |
| 3 | 89.5 |
| 4 | 89 |

TABLE 1-continued

| Sojourn time (minutes) | NTN-Yield (in percent of the theoretical) |
|---|---|
| 5 | 88 |

NTN = Nitrilotriacetonitrile

Reaction temperatures higher than 70°C should be coupled with shorter, and reaction temperatures lower than 70°C should be coupled with longer sojourn times. It has been found, for example, that a reaction temperature of between about 95° and 105°C calls for a sojourn time as short as 5 to 10 seconds to produce good yields of NTN in the following reaction with hydrogen cyanide.

Significant departures from the reaction conditions to be used in the preliminary reaction, for example modification of the reaction temperature and sojourn times, result in poorer NTN-yields. The reaction in the preliminary reactor could not be found in the hydrogen nuclear magnetic resonance spectrum to give rise to the formation of urotropin; the ammonium salt and formaldehyde were found to react in the molar ratio of 1:1, the rate of reaction being a function of time, temperature and concentration. The rate of reaction achieved in the preliminary reaction determines the yield of nitrilotriacetonitrile obtained following the addition of hydrogen cyanide. Too long a sojourn time of the formalin/ammonium salt-mixture, especially at high temperatures, effects reductive alkylation of the ammonium ion by the formaldehyde with the resultant formation of methylamine and formic acid.

Conditional upon the concentration of water in the starting materials, e. g. in the aqueous hydrogen cyanide or formaldehyde solution, the reaction mixture produced in the second reactor contains varying concentrations of nitrilotriacetonitrile. In order to avoid precocious precipitation of the nitrile from the reaction mixture, given a high concentration of nitrile therein, and clogging of the reactor, which may result therefrom, it is necessary to maintain the reactor at certain minimum temperatures, at which the reaction mixture has a liquid consistency. The following Table 2 indicates by way of example the minimum temperatures which are required to be maintained for various NTN-concentrations in the reaction mixture, in the second reactor.

TABLE 2

| % NTN | 10 | 15 | 20 | 25 | 44 |
|---|---|---|---|---|---|
| Temperature(°C) | 92 | 96 | 100 | 102 | 106 |

As the quality, especially the coloration, of the reaction product decreases gradually with an increasing temperature, it is highly desirable that the minimum temperature necessary in each particular case be not significantly exceeded.

The mother liquor, which is obtaind after isolation of the nitrilotriacetonitrile from the reaction mixture, contains sulfuric acid as a further reaction product, and organic by-products, such as glycolic acid nitrile, methylaminodiacetonitrile and methylene-bis-aminodiacetonitrile in a concentration of between about 1 and 2 weight percent. In view of the formation, per unit of weight NTN, of a quantity of mother liquor, 3 to 4 times larger than the quantity of NTN, which cannot simply be delivered to the local waste water disposal system, the step of subjecting the mother liquor to finishing treatment under commercially attractive conditions must be regarded as being an essential operation in the production of NTN. In various earlier processes it has been suggested that the by-product-containing mother liquor be neutralized with ammonia and then recycled to the reactor. This operation, however, is not fully satisfactory as it effects cumulation of the contaminants in the reactor and increasing coloration of the reaction product until black. Needless to say therefore the work-up of mother liquor in accordance with the present invention must be deemed a step forward in the art.

The process of the present invention distinguishes favorably over earlier processes as it enables nitrilotriacetonitrile to be produced continuously in yields not obtainable heretofore and under mild reaction conditions with the resultant formation of a pure colorless product. In addition thereto, it enables the by-products to be worked up, and the excess proportions of starting materials to be recovered, under commercially attractive conditions.

An exemplary embodiment of the process of the present invention will now be described by way of example only and without limitation, with reference to the accompanying flow scheme.

Preliminary reactor 1, which is fitted with a heating jacket and may be a tubular coil reactor, for example, is fed continuously with an aqueous ammonium sulfate solution travelling through conduit 2, and with an aqueous formaldehyde solution travelling through conduit 3. The two solutions are intimately mixed together and reacted in reactor 1 at a temperature of between about 50° and 110°C, within a period of between 2 seconds and 4 minutes. The reaction mixture produced in reactor 1 is delivered through conduit 4 to second reactor 5 which is series-connected to reactor 1. In reactor 5, the reaction mixture coming from reactor 1 is further reacted, with thorough agitation, with hydrogen cyanide in an aqueous acid phase, under a pressure of between 3 and 25 atmospheres (gauge) and at a temperature necessary to liquefy resulting nitrilotriacetonitrile, for a period of at least 3 minutes. The hydrogen cyanide is fed through conduit 6 to reactor 5 which has a shape approaching that of reactor 1. The reaction mixture is taken from reactor 5 through conduit 7, and nitrilotriacetonitrile is isolated therefrom by cooling the mixture in crystallizer 8 with pressure relief down to 8 atmospheres (gauge). This effects precipitation of the nitrile from the aqueous phase. The precipitated nitrile is delivered to separator 9, which communicates with crystallizer 8 through line 10, isolated therein by filtration or centrifugation, and removed through conduit 11. Aqueous mother liquor, which accumulates in separator 9, contains the excess proportions of ammonium sulfate together with sulfuric acid originating from the reaction, and minor proportions of organic by-products. The sulfuric acid and ammonium sulfate in excess are recovered by introducing the mother liquor through conduits 12 and 13 together with an equal amount by volume of an aqueous saturated ammonium sulfate solution travelling through conduit 15, into evaporator 14. In evaporator 14, the mixture is treated under vacuum and a quantity by volume of water, the same as that introduced into the reaction together with the starting materials and formed during the reaction as water of reaction, is evaporated therefrom. Only once, namely at the start of the reaction is the saturated ammonium sulfate solution supplied to the evaporator, as it is later circulated through conduit 13, from separator 25. Water evaporating at the head of evaporator 14 is conveyed through conduit 16 and either supplied to mixing vessel 17, or partially removed through line 18. The liquid acid evaporation residue travels through conduit 19 to neutralization vessel 20 in which a pH of at most 6 is established by the addition of ammonia coming from conduit 21. As a result of this, the sulfuric acid is transformed into ammonium sulfate and then precipitates together with the excess proportion of ammonium sulfate used at the start of the reaction. In centrifuge 22, the ammonium sulfate is separated from the aqueous phase and conveyed through conduit 23 to mixing vessel 17 for making fresh ammonium sulfate solution. Upon centrifugation, mother liquor saturated with ammonium sulfate is obtained from which a minor proportion of an oily phase having the organic by-products therein is separated. To achieve this, the mother liquor is delivered through conduit 24 to separator 25. The by-products are taken from separator 25 through line 26, and mother liquor freed from oily constituents is recycled to the evaporator, through line 13.

EXAMPLE 1

28.75 kg of an aqueous formalin solution having a strength of 30 weight percent and 18.05 kg of an aqueous ammonium sulfate solution having a strength of 42 weight percent were heated to 70°C and supplied, per hour, to preliminary reactor 1, through conduits 2 and 3, respectively. The formaldehyde and ammonium sulfate were used in the molar ratio of 3:0.6. Preliminary reactor 1 was maintained at a temperature of 70°C and under a pressure of substantially 12 atmospheres gauge. The preliminary reactor was a heated tubular coil which had a diameter of 15 mm, a length of 7.7 meters and a volume of 1.36 liters. The sojourn time of the reaction components in preliminary reactor 1 was approximately 2 minutes. The reaction mixture coming from preliminary reactor 1 was mixed, per hour, with 9.7 kg of an aqueous hydrogen cyanide solution with a strength of 80 weight percent, and the resulting mixture was delivered to reactor 5 series-connected to reactor 1. Reactor 5 equally was a heated tubular coil which had a diameter of 15 mm, a length of 38.5 meters and a volume of 6.8 liters. The temperature in reactor 5 was 100°C and the pressure substantially 10 atmospheres gauge. The reaction mixture contained hydrogen cyanide and formaldehyde in the molar ratio of 1:1 and was allowed to remain in reactor 5 for a period of about 8 minutes. Following completion of the reaction and relief of pressure, the hot reaction mixture produced in reactor 5 was conveyed to water-cooled crystallizer 8 which was fitted with an agitator and contained a crystal mash orginating from the process. In crystallizer 8, the nitrilotriacetonitrile — briefly termed NTN hereinafter — was precipitated in the form of fine crystals. The nitrile-containing mash was centrifuged in separator 9. The resulting crystalline nitrile was water-washed, this conditional upon its purity, and may be dried, if desired.

Mother liquor, substantially 43–44 kg/hr, coming from separator 9 was mixed with a saturated ammonium sulfate solution in a ratio by volume of approximately 1:1, and the resulting mixture was fed to circulation evaporator 14. In evaporator 14, the overall quantity of water introduced into the process together with the starting solutions, including the water formed during the reaction to produce NTN, altogether approximately 35.5–36 KgH$_2$O/hr, was evaporated at 55°–60°C under a pressure of between about 120 and 150 mm Hg. Sulfuric acid-concentrate coming from evaporator 14 was treated, with agitation, in water-cooled neutralization vessel 20 by means of gaseous ammonia and a pH-value of between 3 and 4 was established. This effected precipitation of crystalline ammonium sulfate and of a minor proportion of a dark brown oily phase. By means of centrifuge 22 the ammonium sulfate was isolated from the aqueous solution and oil, and dissolved in mixing vessel 17 with water. This gave a solution with a strength of 42 percent by weight, which was recycled to preliminary reactor 1. The saturated ammonium sulfate solution coming from centrifuge 22 was freed from oil in separator 25 and delivered to circulation evaporator 14, together with mother liquor coming from separator 9. The oil, which was obtained at a rate of between about 0.6 and 0.8 kg/hr, was destroyed.

11.8–11.95 kg of NTN were obtained per hour for a conversion rate of 98 percent. The NTN-yield accordingly was 92 to 93 %, based on the quantity of HCN or CH$_2$O used, or 93.8–94.9 %, based on the hydrogen cyanide or formaldehyde which underwent conversion. The NTN melted at 128°C.

EXAMPLE 2

2.9 kg of an aqueous formaldehyde solution with a strength of 30 weight percent and 1.78 kg of an aqueous ammonium sulfate solution with a strength of 41.5 weight percent, preheated to 70°C, were continuously supplied, per hour, to preliminary reactor 1. The formaldehyde and ammonium sulfate were used in the molar ratio of 3:0.58, corresponding to an ammonium sulfate excess of 16 %. Preliminary reactor 1 was also preheated to 70°C. The reactor had a volume of 134 cubic centimeters and the starting components were allowed to remain therein for a period of 2 minutes. The reaction mixture coming from preliminary reactor 1 was delivered to the base portion of second reactor 5, which was a glass tube disposed in upright position. The glass tube had a diameter of 45 mm, a height of 700 mm and was fitted with a heating jacket. The base of reactor 5, maintained at a temperature of 70°C, was fed simultaneously with 0.98 kg/hr of an aqueous hydrogen cyanide solution with a strength of 80 weight percent, by means of a frit. The molar ratio of CH$_2$O:HCN was 1:1. The reaction mixture was allowed to remain in reactor 5 for a period of between 8 and 9 minutes and reached a temperature of 75°–80°C at the upper end of the reactor. The reaction mixture was conveyed from reactor 5 to two heated agitator vessels in cascade arrangement, heated to 70°C, and NTN was directly precipitated from the reaction mixture. At the end of 4 hours, the reaction mixture was in crystallizer 8, in which it was cooled down to 12°–15°C. The resulting NTN-crystals were isolated, water-washed and dried. The mother liquor obtained following isolation of the crystals was worked up in a manner analogous to that described in Example 1.

1.2 kg/hr of colorless NTN, which melted at 128°C, were obtained for a 97–98 % conversion of HCN or CH$_2$O. This corresponded to a yield of 92.5%, based on the quantity of HCN or CH$_2$O used, or 94.3–95.4 %, based on the HCN or CH$_2$O which underwent conversion.

EXAMPLE 3

The procedure was the same as that described in Example 2, save that reactor 1 used for preliminary reaction of formaldehyde with ammonium sulfate had a volume of 67 cubic centimeters. This gave a 1-minute sojourn time for the starting components. The yield was 1.165 k/hr of NTN, or 90 %, based on the quantity of $CH_2O$ or HCN used.

EXAMPLE 4

The procedure was the same as that described in Example 2, save that the preliminary reactor had a volume of 201 cubic centimeters. This gave a sojourn time of 3 minutes. The yield was 1.160 kg/hr of NTN, or 89.5 %, based on the quantity of $CH_2O$ or HCN used.

EXAMPLE 5

The procedure was the same as that described in Example 2, save that preliminary reactor 1 had a volume of 335 cubic centimeters. This gave a sojourn time of 5 minutes. The yield was 1.140 kg/hr of NTN, or 88 %, based on the quantity of $CH_2O$ or HCN used.

EXAMPLE 6: (Comparative Example)

Yellow colored mother liquor containing sulfuric acid, which had a color index of between 2 and 3 (Gardner scale) and was obtained at the rate of 4.35 kg/hr following separation of crystalline NTN as described in Example 2, was concentrated at about 70°C and under a pressure of 200 mm Hg in an evaporator with evaporation of water. Following this, the mother liquor was treated with ammonia so as to establish a pH-value of 3 to 4 and the liquor was supplied at the rate of 1.78 kg/hr to the preliminary reactor for reaction with formaldehyde therein. The reaction mixture coming from the preliminary reactor was reacted with hydrogen cyanide in a manner analogous to that described in Example 2. 1.21 kg/hr of colorless NTN were obtained. The NTN-yield was 93.4 %, based on the quantity of formaldehyde used.

Following this circulation, dark-colored mother liquor, which had a color index of 5, was obtained once again, from which a dark-brown oil precipitated upon neutralization with $NH_3$. This operation showed that the continuous circulation of mother liquor without purification was unsatisfactory. By-products formed during the process were carried along and they contributed to contamination or coloration of the final product.

EXAMPLE 7

A solution was produced from formalin with a strength of 30 weight percent and sulfuric acid with a strength of 96 weight percent in a ratio by weight of 29:5.92, and placed in a reservoir. By means of a dosing pump, the solution was continuously taken from the reservoir at the rate of 34.9 kg/hr, cooled to 12°C, and supplied to a mixing chamber which was maintained under a pressure of approximately 15 atmospheres gauge. The mixing chamber was fed simultaneously with 1.97 kg/hr of liquid ammonia, which was fed at a rate such that the molar ratio of $NH_3:H_2SO_4$ always was 1:0.5. The reaction mixture reached a temperature of approximately 100°C. After a sojourn time of 3 seconds in the chamber, the reaction mixture was rapidly cooled, within 5 seconds, down to substantially 45°C by conveying it through a cooling pipe. At this temperature, the reaction mixture travelled through the preliminary reactor within 1.3 minutes.

Following this, an aqueous hydrogen cyanide solution with a strength of 80 weight percent was added to the reaction mixture coming from the preliminary reactor. The solution was added at such a rate that the molar ratio of $CH_2O:HCN$ was maintained at 1:1 (9.8 kg 80 % HCN/hr). The resulting reaction mixture was then passed through the second reactor which was a heated tubular coil. The coil had a diameter of 15 mm and a length of 38.5 meters, and the reaction to NTN was effected therein within a period of 9.5 minutes, at 105°C and under a pressure of 12 atmospheres gauge. Under these conditions, the NTN remained dissolved in the mother liquor. The pressure prevailing in the tubular coil was maintained by means of a pressure-retaining valve disposed at the end of the coil. The valve was also used to effect pressure relief and the reaction mixture was delivered to a water-cooled agitator vessel, which was used as a crystallizer and contained a charge of crystal mash having a temperature of 20°C, originating from the process. This effected precipitation of crystalline NTN. A quantity of material, corresponding to that supplied within the same period of time, was periodically taken, at intervals of about 30 minutes, from the crystallizer and delivered to a centrifuge, in which the crystals were isolated. The isolated NTN was water-washed and dried at 70°C, for determination of the yield. 11.85 kg/hr of colorless NTN (melting point = 128°C) were obtained for a HCN or $CH_2O$-conversion rate of 97 %. This corresponded to a yield of 91.5 %, based on the quantity of HCN or $CH_2O$ used, or 94.4 %, based on the HCN or $CH_2O$ which underwent conversion.

EXAMPLE 8: (Comparative Example)

The procedure was the same as that described in Example 7 save that the formalin/sulfuric acid-mixture was heated to 70°C prior to entering the mixing chamber. In addition thereto, the mixing chamber and the mixture were heated in the following sojourn zone of the chamber to a temperature of 70°C by means of hot water. A temperature of between about 160° and 170°C was found to establish in the mixing chamber upon the supply of ammonia. NTN was obtained in a yield of 7.25 kg/hr or 56 %.

The mother liquor was found to contain significant proportions of methylaminodiacetonitrile, as determined by hydrogen nuclear magnetic resonance spectroscopy.

The methylaminodiacetonitrile was extracted by means of methylene chloride. Gas chromatographic analysis indicated that the compound was formed at the rate of 2.76 kg/hr or 35 %, based on the formaldehyde used.

We claim:

1. Process for the manufacture of nitrilotriacetonitrile by reacting an ammonium salt of sulfuric acid, phosphoric acid or hydrochloric acid with an aqueous formaldehyde solution having a strength of between about 20 and 55 weight percent and liquid hydrogen cyanide or an aqueous solution thereof, having a strength of at least 40 weight percent, at a temperature of between about 50° and 110°C., completing the reaction and separating the reaction mixture into firstly crystalline nitrilotriacetonitrile and secondly an aqueous acid mother liquor which comprises A. continuously supplying a preliminary reactor with a substantially saturated aqueous solution of the ammonium salt and the aqueous methanol-free formaldehyde solution, which are preheated at a temperature of between about 50° and 110°C., the ammonium salt being used in a stoichiometric excess between 5 and 40 percent over the formaldehyde;

thoroughly mixing the said aqueous solution components and reacting them inside the said preliminary reactor at a temperature of between about 50° and 110°C. and within a period of between about 2 seconds and 4 minutes;

B. delivering the resulting reaction product to a second reactor series-connected to the said preliminary reactor and reacting the said reaction product in the said second reactor with a stoichiometric proportion, based on the amount of the formaldehyde, of liquid hydrogen cyanide or with the aqueous solution thereof, for a period between about 3 and 10 minutes, under a pressure between 3 and 25 atmospheres gauge and at a temperature between about 90° and 110°C. with the resultant formation of nitrilotriacetonitrile and the free acid of the ammonium salt;

C. withdrawing the reaction mixture from the said second reactor and quenching it by cooling down to a temperature between about 20° and 30°C. with pressure relief to atmospheric pressure and isolating the precipitated nitrilotriacetonitrile from the reaction mixture by filtration or centrifugation.

2. The process as claimed in claim 1, wherein the ammonium salt is used in a stoichiometric excess of between about 15 and 20 percent.

3. The process as claimed in claim 1, wherein the preliminary reactor is operated at a reaction temperature of between about 60° and 70°C.

4. The process as claimed in claim 1, wherein the reaction components are allowed to remain in the preliminary reactor for a period of time of between about 1 and 2 minutes.

5. The process as claimed in claim 1, wherein the reaction with hydrogen cyanide is effected under a pressure of between about 10 and 15 atmospheres gauge.

6. The process as claimed in claim 1, wherein the reaction components are allowed to remain in the second reactor for a period of time of between about 6 and 10 minutes.

7. The process as claimed in claim 1, wherein the acid and the excess proportion of the ammonium salt introduced into the reaction together with the starting materials are recovered by mixing the aqueous phase or mother liquor freed from nitrilotriacetonitrile with a substantially equal proportion by volume of a saturated aqueous formaldehyde solution, which is the same as that used as starting material; treating the resulting mixture under vacuum to evaporate water therefrom in a quantity by volume, which is substantially the same as that introduced into the process together with the starting materials and that formed in the process as reaction water; treating the liquid acid evaporation residue with ammonia so as to establish a pH-value of between 3 and 5, freeing the said evaporation residue from ammonium salt which commences to precipitate; transforming the said ammonium salt into an aqueous solution; and recycling the said aqueous solution to the preliminary reactor.

8. The process as claimed in claim 7, wherein the aqueous evaporation residue freed from solid ammonium salt is further freed from oily by-products originating from the reaction, and the remaining aqueous proportion of the said residue is introduced together with fresh mother liquor freed from nitrilotriacetonitrile, into the evaporation zone.

* * * * *